United States Patent
Cha et al.

(10) Patent No.: US 11,912,787 B2
(45) Date of Patent: Feb. 27, 2024

(54) PEPTIDE FOR SKIN AGING PREVENTION AND WRINKLE REDUCTION, AND COMPOSITION COMPRISING SAME

(71) Applicant: DERMAFIRM, INC., Wonju-si (KR)

(72) Inventors: Hoon Cha, Wonju-si (KR); Young Il Kwon, Wonju-si (KR); Sang Cheol Han, Wonju-si (KR); Jin Wook Kim, Wonju-si (KR); Mi Young Lee, Wonju-si (KR); Ga Hee Hur, Wonju-si (KR)

(73) Assignee: DERMAFIRM, INC., Wonju-si (KR)

( * ) Notice: Subject to any disclaimer, the term of this patent is extended or adjusted under 35 U.S.C. 154(b) by 254 days.

(21) Appl. No.: 17/422,494

(22) PCT Filed: Jan. 22, 2020

(86) PCT No.: PCT/KR2020/001055
§ 371 (c)(1),
(2) Date: Jul. 13, 2021

(87) PCT Pub. No.: WO2020/159143
PCT Pub. Date: Aug. 6, 2020

(65) Prior Publication Data
US 2022/0073562 A1    Mar. 10, 2022

(30) Foreign Application Priority Data
Jan. 28, 2019    (KR) .......................... 10-2019-0010707

(51) Int. Cl.
| | |
|---|---|
| *C07K 7/06* | (2006.01) |
| *C07K 19/00* | (2006.01) |
| *A61K 38/06* | (2006.01) |
| *A61K 38/08* | (2019.01) |
| *A61K 8/64* | (2006.01) |
| *A61Q 19/08* | (2006.01) |
| *A61P 17/00* | (2006.01) |
| *C07K 5/083* | (2006.01) |
| *C07K 5/103* | (2006.01) |
| *A61K 38/00* | (2006.01) |

(52) U.S. Cl.
CPC .............. *C07K 5/0806* (2013.01); *A61K 8/64* (2013.01); *A61Q 19/08* (2013.01); *C07K 5/1008* (2013.01); *C07K 19/00* (2013.01); *A61K 38/00* (2013.01)

(58) Field of Classification Search
CPC ........ C07K 5/0806; C07K 7/06; C07K 19/00; C07K 5/1008; A61K 8/64; A61K 38/06; A61K 38/08; A61Q 19/08; A61P 17/00
See application file for complete search history.

(56) References Cited

U.S. PATENT DOCUMENTS

| 2011/0250153 A1 | 10/2011 | Lili et al. |
| 2017/0143604 A1 | 5/2017 | Idkowiak-Baldys et al. |

FOREIGN PATENT DOCUMENTS

| KR | 10-2006-0015597 A | 2/2006 |
| KR | 10-2016-0084540 A | 7/2016 |

OTHER PUBLICATIONS

Pickart et al., "Anti-Aging Activity of the GHK Peptide—The Skin and Beyond," Journal of Aging Research & Clinical Practice, 2012, 1: 13-16. (Year: 2012).*
Hur et al., "Effect of oligoarginine conjugation on the antiwrinkle activity and transdermal delivery of GHK peptide," Journal of Peptide Science, Feb. 2020, 26(2): e3234, pp. 1-10 enclosed. (Year: 2020).*
Lintner, K. et al. "Biologically Active Peptides: From a Laborator Bench Curiosity to a Functional Skin Care Product", International Journal of Cosmetic Science, 2000, vol. 22, pp. 207-218.

* cited by examiner

*Primary Examiner* — Julie Ha
(74) *Attorney, Agent, or Firm* — Bridgeway IP Law Group, PLLC; Jihun Kim

(57) ABSTRACT

Proposed is a peptide for skin anti-aging and anti-wrinkle, comprising a glycine-histidine-lysine tripeptide and polyarginine linked to the carboxy-terminus of the tripeptide, and a composition for skin anti-aging and anti-wrinkle comprising the peptide. The peptide and composition may enter the cytoplasm more rapidly and efficiently than a conventional GHK tripeptide, and may exhibit skin anti-aging and anti-wrinkle effects similar to those of the GHK tripeptide even at a lower concentration than that of the GHK tripeptide.

6 Claims, 4 Drawing Sheets
Specification includes a Sequence Listing.

Figure 1. Cytotoxicity of GHK-acetate, GHK-R4 and Pal-GHK-R4 on Hs68 fibroblast cells. Cell viability was determined by MTT assay.

Figure2. The comparison of cellular uptake of GHK-acetate and GHK-R4 in Hs68 fibroblast. The cells were treatde with 50μM GHK-acetate and GHK-R4 for 1 hr and 3 hr. GJK-R4 showed faster cell permeation than GHK-acetate.

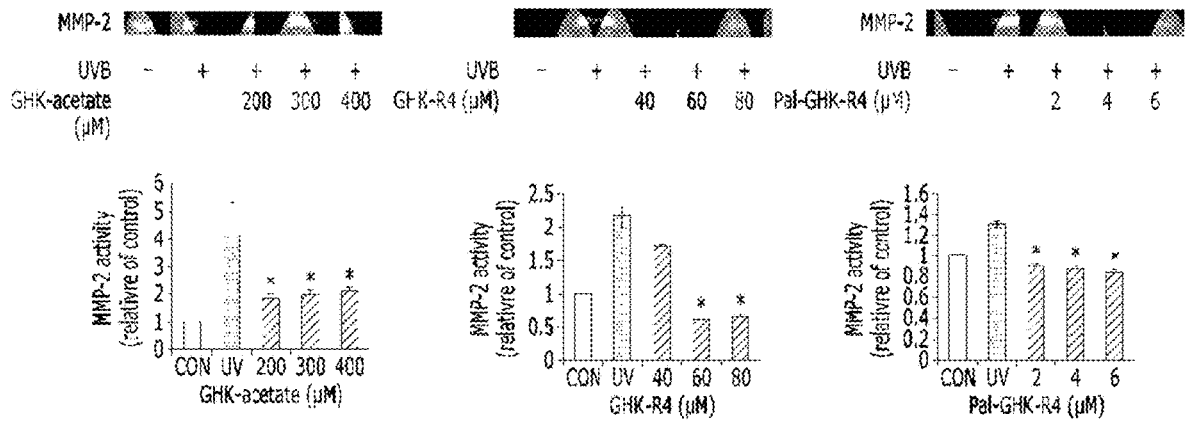

Figure 3. The effect of GHK-acetate, GHK-R4 and Pal-GHK-R4 on MMP-2 activity was analyzed by gelatin zymography. Results are expression as mean ±SD of independent three tests. *p<0.05 compared with UVB-irradiation control.

FIG. 3

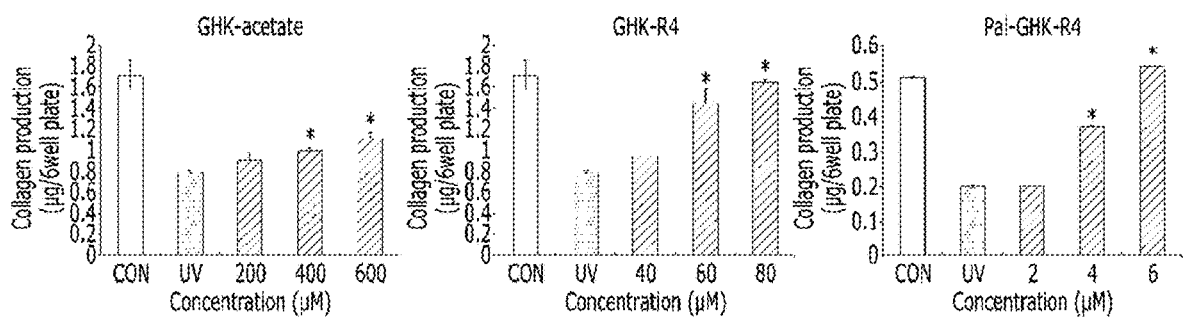

Figure 4. The effect of GHK-acetate, GHK-R4 and Pal-GHK-R4 on collagen production was analyzed by collagen assay, collagen synthesis increased in a concentration-dependent manner. *p<0.05 compared with UVB-irradiation control.

FIG. 4

Figure 5. The effect of GHK-acetate, GHK-R4 and Pal-GHK-R4 on MMP-9 expression. $p<0.05$, $P<0.01$ compared with UVB-irradiation control.

PEPTIDE FOR SKIN AGING PREVENTION AND WRINKLE REDUCTION, AND COMPOSITION COMPRISING SAME

INCORPORATION OF SEQUENCE LISTING

This application contains a sequence listing submitted in Computer Readable Form (CRF). The CFR file containing the sequence listing is entitled "2-PJK4964832-SQListing.txt", which was created and modified on Nov. 20, 2023, and is 4,096 bytes in size. The information in the sequence listing is incorporated herein by reference in its entirety.

TECHNICAL FIELD

The present invention relates to a peptide for skin anti-aging and anti-wrinkle and a composition comprising the same, and more particularly, to a peptide for skin anti-aging and anti-wrinkle, the peptide comprising a glycine-histidine-lysine tripeptide and polyarginine linked to the carboxy-terminus of the tripeptide, and a composition for skin anti-aging and anti-wrinkle comprising the peptide.

BACKGROUND ART

The term "peptide" refers to a substance in which amino acids, which are protein components, are linked by peptide bonds, and which comprises about 2 to 50 amino acid residues. Peptide drugs are made by selecting the smallest unit having a desired physiological activity among proteins. These peptide drugs that target a specific molecule or a specific signaling system are biocompatible and have specific activity, and thus they can exhibit strong pharmacological activity while having few side effects, and have been found to be highly successful in clinical trials for new drug development compared to low-molecular-weight compounds. In addition, peptide drugs have advantages in that they are easily produced and modified using 20 kinds of amino acids as peptide components, and thus quality control and industrialization thereof are easy. Accordingly, a variety of new peptide drugs have been developed for the purpose of treating diseases and cosmetic problems.

Examples of peptide drugs include a glycine-histidyl-lysine tripeptide (hereinafter referred to as GHK), also called tripeptide-1. GHK is a peptide originally present in human plasma, saliva and urine in small amounts. GHK is present in the plasma at a concentration of about 200 ng/ml at the age of 20, and then the concentration of GHK decreases to 80 ng/ml at the age of 60. It has been found that the timing of this decrease is consistent with the timing of the distinct decrease in in vivo production of GHK caused by aging. GHK has been reported to have various effects related to skin regeneration, such as wound healing, enhancement of fixation of skin graft, anti-inflammatory activity, and promotion of blood vessel formation.

It is difficult for a peptide drug to penetrate the lipid membrane surrounding individual cells due to their hydrophilicity. Thus, when the target of the drug is present in cells, a strategy allowing the drug to pass through the plasma membrane is required, which allows the drug to pass through the epithelium or endothelium, which is connected by tight junctions to the oral cavity, nasal cavity, lungs or brain to form dense barriers. Various strategies for delivering peptide drugs into cells have been developed, and examples thereof include methods employing cell penetrating peptides (CPPs), viral nanoparticles (or virus-like particles), liposomes or exosomes, DNA nanoclew, carbon nanotube, silica nanoparticles, gold nanoparticles, or the like.

Since the GHK tripeptide is also a hydrophilic peptide which hardly penetrates cells, and several molecular modifications have been developed to overcome this disadvantage. For example, Lintner and Peschard (Int J Cosmet Sci. 2000 June; 22(3):207-18) elucidated that the ability of GHK to penetrate cells could be increased by about 100 to 10,000 times by attaching a lipophilic palmitoyl group to GHK (hereinafter referred to as pal-GHK). However, pal-GHK showed a similar level of effect in the same concentration range as GHK to which a palmitoyl group was not attached, indicating that the above-described modification did not lead to an increase in the effect. In addition, Lim et al. (J Cosmet Sci. 2003 September-October; 54(5):483-91) attached 9 lysines known as CPP to the amino-terminus of GHK ($K_9$-GHK, SEQ ID NO.: 1), and also reported that $K_9$-GHK also showed a similar level of effect on cells at the same concentration as GHK.

That is, there is an invention that increases the penetration ability of GHK by molecular modification, but there has not been disclosed a molecular modification that can improve the effect of GHK while increasing the penetration ability thereof, in particular, a peptide in which polyarginine is linked to the carboxy-terminus of a tripeptide. Thus, the effect of this modified peptide also has not yet been revealed.

DISCLOSURE

Technical Problem

The present invention has been made in order to satisfy the above needs, and one embodiment of the present invention provides a peptide for skin anti-aging and anti-wrinkle comprising: a glycine-histidine-lysine tripeptide; and polyarginine linked to the carboxy-terminus of the tripeptide.

Another embodiment of the present invention provides a composition for skin anti-aging and anti-wrinkle comprising the peptide.

Still another embodiment of the present invention provides a method for skin anti-aging and anti-wrinkle comprising a step of administering to a subject the composition comprising the peptide.

The technical problems to be achieved by the present invention are not limited to the above-mentioned technical problems, and other technical problems not mentioned herein will be clearly understood by those skilled in the art to which the present invention belongs from the following description.

Technical Solution

To achieve the above technical problems, a peptide for skin anti-aging and anti-wrinkle according to one aspect of the present invention comprises: a glycine-histidine-lysine tripeptide; and polyarginine linked to the carboxy-terminus of the tripeptide.

Here, a lipophilic acyl functional group may be linked to the amino-terminus of the peptide.

The acyl functional group may contain 1 to 15 carbon atoms.

The acyl functional group may be a covalently bonded lipophilic group comprising three or more carbon atoms. The acyl functional group may be any one group selected from among propionyl, caproyl, lauryl, myristoyl, palmitoyl, stearoyl, oleyl, eicosanoyl, docosanoyl, acetyl, propyl, hexyl, dodecyl, myristyl, hexadecyl, octadecyl, eicosanyl, and docosanyl.

The polyarginine may comprise 2 to 8 arginines linked together.

A composition for skin anti-aging and anti-wrinkle according to another aspect of the present invention comprises the peptide.

Here, the composition may comprise 0.1 to 1000 μM of the peptide. The peptide in the composition may not comprise a lipophilic group, and the composition may comprise 10 to 1,000 M of the peptide. The peptide in the composition may comprise a lipophilic group, and the composition may comprise 0.1 to 10 μM of the peptide. In addition, the peptide may be comprised in an amount of 10 ppm (0.001%) to 100,000 ppm (10%) based on the total weight of the composition.

The composition may further comprise a pharmaceutically or cosmetically acceptable carrier.

The composition may have a formulation selected from the group consisting of solution, external ointment, cream, foam, nutrient lotion, skin softener, pack, skin lotion, emulsion, makeup base, essence, soap, liquid cleanser, bath soak, sunscreen cream, sun oil, suspension, emulsion, paste, gel, lotion, powder, surfactant-comprising cleanser, oil, powder foundation, emulsion foundation, wax foundation, patch, and spray formulations.

A method for skin anti-aging and anti-wrinkle according to the present invention comprises a step of administering the composition comprising the peptide to a subject.

The subject may be an experimental animal such as a human or a rodent (e.g., rat, mouse or guinea pig), and may be a subject in need of skin anti-wrinkle and anti-aging.

The administration may be transdermal administration. As used herein, the term "transdermal administration" means that an effective amount of the active ingredient comprised in the pharmaceutical composition is delivered into the skin by topical administration to the skin The above-described means for solving the problems are intended to be merely exemplary and should not be construed as limiting the present invention. In addition to the exemplary embodiments described above, additional embodiments may exist in the accompanying drawings and the detailed description.

Advantageous Effects

The present invention discloses a novel peptide comprising a glycine-histidine-lysine tripeptide, polyarginine (hereinafter referred to as R4, SEQ ID NO.: 2) linked to the carboxy-terminus of the tripeptide, and a lipophilic group covalently bonded to the amino-terminus of the tripeptide, and also discloses the improved effects of the peptide on the skin, and a composition comprising the peptide.

The peptide according to an embodiment of the present invention and the composition comprising the peptide may enter the cytoplasm more rapidly and efficiently than GHK. The peptide and composition thus introduced have the effects of inhibiting the activity of, particularly, proteases whose expression is increased by UV rays, and restoring collagen synthesis inhibited by UV rays.

In addition, since the peptide and composition according to the present invention easily enter the cytoplasm, they may have skin anti-aging and anti-wrinkle effects similar to those of GHK even when used at lower concentrations than GHK, and thus are economical. In addition, the peptide and the composition may be advantageously used for a long period of time because they have almost no cytotoxicity even at high concentrations.

It should not be understood that the effects of the present invention are not limited to the above-described effects and include all effects that can be inferred from the features of the invention described in the detailed description of the present invention and the appended claims.

BRIEF DESCRIPTION OF DRAWINGS

FIG. 3 compares the effects of GHK and the peptides of the present invention on UV-induced MMP-2 activity.

FIG. 4 compares the effects of GHK and the peptides of the present invention on collagen synthesis in UV-irradiated cells.

MODE FOR INVENTION

Figure 1:
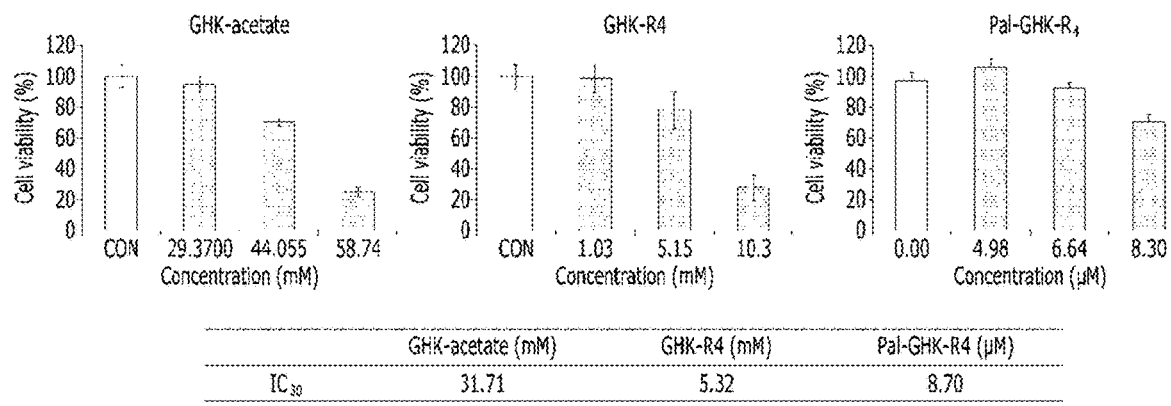
FIG. 1 compares the effects of GHK and the peptides of the present invention on cells.

Hereinafter, the present invention will be described in more detail. However, the present invention may be embodied in various different forms, and the scope of the present invention is not limited by the embodiments described herein, and is defined only by the appended claims.

In addition, the terms used in the present invention are only intended to describe specific embodiments, and are not intended to limit the present invention. Singular expressions include plural expression unless the context clearly indicates otherwise. Throughout the specification of the present invention, it is to be understood that when any part is referred to as "comprising" any component, it does not exclude other components, but may further comprise other components, unless otherwise specified.

Additionally, amino acids present in any peptide that is described in the present invention may be L-amino acids or D-amino acids. Preferably, the amino acids may be L-amino acids.

A peptide for skin anti-aging and anti-wrinkle according to one aspect of the present invention comprises: a glycine-histidine-lysine tripeptide; and polyarginine linked to the carboxy-terminus of the tripeptide.

The glycine-histidine-lysine tripeptide (hereinafter referred to as GHK) has been reported to have various skin regeneration-related effects as described above. In particular, GHK is known to increase the synthesis of substances constituting the extracellular matrix, such as collagen, elastin, and glycosaminoglycan, in fibroblasts. This extracellular matrix is a major component of the skin and can serve as a protective layer and a matrix that supports the growth of new fibroblasts to grow. When the extracellular matrix of the skin decreases, wrinkles increase and deepen, and the skin shows aged conditions such as sagging.

Here, the polyarginine (Rx, where x=the number of arginines) may comprise 2 to 8 arginines linked together, preferably 4 to 8 arginines linked together, most preferably 4 arginines linked together. Polyarginine is known as a cell penetrating peptide. More specifically, it has been reported that polyarginines comprising 6 to 15 arginines has cell penetration effects in proportion to the number of arginine, and when polyarginine comprising 5 or less arginines hardly penetrate cells. The present inventors have found that, when polyarginine is linked to the carboxy-terminus of the tripeptide, polyarginine comprising four arginines can also enhance cell penetration.

The peptides for anti-aging and anti-wrinkle include a peptide comprising a GHK tripeptide, which comprises L-amino acids or D-amino acids, and polyarginine linked to the carboxy-terminus of the tripeptide, as well as retro-inverso analogues of the peptide. The term "retro-inverso analogue" refers to an analogue in which the amino acid sequence is reversed with respect to a specific peptide and the molecular chirality of the alpha center of each amino acid is also inverted. In particular, a retro-inverso analogue of a peptide composed of L-amino acids is not easily degraded, and thus more stable than the peptide. When the retro-inverso analogue is well designed, it may exhibit the same efficacy as the original peptide by interaction with the target of the original peptide.

The peptide may comprise a lipophilic acyl functional group (RCO—) covalently bonded to the amino-terminus of the peptide, and R of the acyl functional group may be a linear or branched chain alkyl or alkenyl group having 1 to 15 carbon atoms. The lipophilic may be any one group selected from among propionyl, caproyl, lauryl, myristoyl, palmitoyl, stearoyl, oleyl, eicosanoyl, docosanoyl, acetyl, propyl, hexyl, dodecyl, myristyl, hexadecyl, octadecyl, eicosanyl and docosanyl. Preferably, the lipophilic may be a palmitoyl group. The lipophilic group may be derived from an unsaturated or saturated fatty acid. The lipophilic group may be linked to the amine group of the amino-terminus or to the side-chain amine group of lysine. Preferably, the lipophilic group may be linked to the amine group of the amino-terminus.

The peptide may have skin anti-aging and anti-wrinkle effects. The biggest cause of skin aging has been reported to be UV rays, and it is known that UV rays degrade extracellular matrix components such as collagen, and increase the expression of matrix metalloproteinase (MMP), which mainly degrades the extracellular matrix. The peptide according to one aspect of the present invention may decrease the expression and activity of MMP that increased by UV rays, and may increase collagen synthesis that decreased by UV rays. This increase in collagen synthesis can reduce wrinkles and prevent skin aging. In particular, compared to GHK which is known to have anti-aging and anti-wrinkle effects, GHK-Rx without or comprising a lipophilic group according to one aspect of the present invention may have improved intracellular penetration ability, and may exhibit skin anti-aging and anti-wrinkle effects similar to those of GHK even at lower concentrations.

The peptide according to one aspect of the present invention may be produced according to a peptide synthesis method known in the art. The peptide synthesis method is broadly divided into a chemical synthesis method and a biological synthesis method. The peptide according to one aspect of the present invention is preferably produced according to a chemical synthesis method, most preferably a solid-state synthesis method. The biological synthesis method includes a method of introducing a nucleotide sequence encoding a desired peptide into a protein expression vector by a genetic engineering technique, inducing expression of the nucleotide sequence in bacteria, and then isolating the nucleotide sequence.

A composition for skin anti-aging and anti-wrinkle according to another aspect of the present invention comprises the peptide.

Here, the composition may comprise 0.1 to 1000 μM of the peptide. The peptide in the composition may not comprise a lipophilic group, and the composition may comprise 10 to 1,000 M of the peptide. The peptide in the composition may comprise a lipophilic group, and the composition may comprise 0.1 to 10 μM of the peptide. The composition comprising the lipophilic group may exhibit the same effect even at a relatively low concentration. This is because, if the content of the peptide in the composition is excessively low, the peptide may not have sufficient skin anti-aging and anti-wrinkle effects, and if the content of the peptide is excessively high, the peptide may have cytotoxicity.

When the composition is a cosmetic composition, it may comprise the peptide in an amount of 10 ppm (0.001% by weight) to 100,000 ppm (10% by weight) based on the total weight of the cosmetic composition.

Additionally, the peptide may be in a non-copper-bound form. The peptide may be in a copper-bound form, and in this case, the ratio of copper to the peptide may be 1:2. GHK may have an affinity for copper by the amine group (i.e., glycine) of the amino terminus and the side chains of histidine and form a complex with copper, but may have physiological activity without copper. In particular, when a lipophilic group is linked to the amino-terminus of GHK, the GHK may exhibit an effect similar to that of GHK to which the lipophilic group has not been linked, even though the affinity thereof is lowered due to a decrease in the contribution of the amine group to copper binding as described above.

The composition according to one aspect of the present invention may further comprise various pharmaceutically or cosmetically acceptable salts, carriers, excipients, vehicles, and other additives capable of further enhancing the skin anti-aging and anti-wrinkle effects, in addition to the peptide.

The composition may further comprise suitable carriers, excipients and diluents, which are commonly used in the preparation of pharmaceutical compositions. For use, the composition of the present invention may be formulated as oral dosage forms such as powders, granules, tablets, capsules, suspensions, emulsions, or syrups, or in the form of aerosols, external preparations, suppositories, or sterile injectable solutions, according to conventional methods. Carriers, excipients and diluents that may be comprised in the composition include lactose, dextrose, sucrose, sorbitol, mannitol, xylitol, erythritol, maltitol, starch, gum acacia, alginate, gelatin, calcium phosphate, calcium silicate, cellulose, methyl cellulose, microcrystalline cellulose, polyvinylpyrrolidone, water, methylhydroxy benzoate, propylhydroxybenzoate, talc, magnesium stearate, and mineral oil. The composition of the present invention may be formulated using diluents or excipients, such as a filler, an extender, a binder, a wetting agent, a disintegrant and a surfactant, which are commonly used. For the composition according to the present invention, the multifunctional skin-penetrating peptide as an active ingredient is preferably in a transdermal dosage form.

The composition may further comprise one or more cosmetically acceptable carriers which are used in common skin cosmetics, and may be appropriately blended with, for example, but not limited to, an oil, water, a surfactant, a moisturizer, a lower alcohol, a thickener, a chelating agent, a colorant, a preservative, a fragrance, and the like.

The composition may have a formulation selected from the group consisting of solution, external ointment, cream, foam, nutrient lotion, skin softener, pack, skin lotion, emulsion, makeup base, essence, soap, liquid cleanser, bath soak, sunscreen cream, sun oil, suspension, emulsion, paste, gel, lotion, powder, surfactant-containing cleanser, oil, powder foundation, emulsion foundation, wax foundation, patch, and spray formulations.

Hereinafter, examples of the present invention will be described in detail so that the present invention may be easily carried out by those skilled in the art to which the present invention pertains. However, the present invention may be embodied in various different forms and is not limited to the examples described herein.

Novel peptides according to the present invention were synthesized by a solid-state peptide synthesis method, and the synthesized peptides were analyzed by HPLC and LC-MS.

Example 1. Synthesis of H-Arg(Pbf)Arg(Pbf)Arg(Pbf)Arg(Pbf)-CTL-Resin a. Synthesis of H-Arg(Pbf)-CTL resin: 7 g (10 mmol) of 2-chlorotrityl chloride resin (BeadTech, 1% DVB cross-linked, 100 to 200 mesh, 1.41 mmol/g) was placed in a reactor and 40 mL of MC was added thereto, followed by stirring for 30 minutes. The solvent was removed, and 40 mL of DMF was added to the reactor, followed by stirring for 30 minutes. The solvent was removed aging. 6.4 g (1 eq.) of Fmoc-Arg(Pbf)-OH, 40 mL of DMF and 5.3 mL (3 eq.) of DIPEA were placed in the reactor and allowed to react, and then the reaction solution was filtered, washed with 40 mL of DMF, and then capped with 40 mL of a solution of MC:MeOH:DIPEA (17:2:1). After 1 hour of reaction, the reaction solution was filtered and then subjected twice to deprotection reaction using 40 mL of 20% piperidine/DMF solution for 30 minutes each time. The reaction solution was filtered and washed three times with 40 mL of DMF and once with 40 mL of MC.

b. Synthesis of H-Arg(Pbf)Arg(Pbf)-CTL resin: 8.4 g (1.3 eq.) of Fmoc-Arg(Pbf)-OH, 2.0 g (1.3 eq.) of HOBt and 5.7 g (1.5 eq.) of HBTU, each dissolved in 20 mL of DMF, were added to the H-Arg(Pbf)-CTL resin synthesized in step a, and 5.2 mL (3 eq.) of DIPEA was added thereto, followed by reaction. After 3 hours of reaction, completion of the reaction was checked by a Kaiser test, and then the reaction solution was filtered and then subjected twice to deprotection reaction using 40 mL of 20% piperidine/DMF solution for 30 minutes each time. The reaction solution was washed three times with 40 mL of DMF and once with 40 mL of MC, thereby synthesizing H-Arg(Pbf)Arg(Pbf)-CTL resin.

c. Synthesis of H-Arg(Pbf)Arg(Pbf)Arg(Pbf)Arg(Pbf)-CTL resin by continuous reactions: The H-Arg(Pbf)Arg(Pbf)-CTL resin synthesized in step b was reacted with Fmoc-Arg(Pbf)-OH in the same manner as in step b. After completion of the reaction was checked by a Kaiser test, H-Arg(Pbf) was introduced into the reaction product by deprotection reaction, followed by two continuous reactions, thereby synthesizing H-Arg(Pbf)Arg(Pbf)Arg(Pbf)Arg(Pbf)-CTL resin.

Example 2. Synthesis of Boc-GlyHis(Trt)Lys(Boc)-Arg(Pbf)Arg(Pbf)Arg(Pbf)Arg(Pbf)-CTL Resin a. A small amount of MC was added to the H-Arg(Pbf)Arg(Pbf)Arg(Pbf)Arg(Pbf)-CTL resin synthesized in Example 1, and then 6.1 g (1.3 eq.) of Fmoc-Lys(Boc)-OH, 2.0 g (1.3 eq.) of HOBt and 5.7 g (1.5 eq.) of HBTU, each dissolved in 20 mL of DMF, were added thereto and 5.2 mL (3 eq.) of DIPEA was added thereto, followed by reaction. After 4 hours of reaction, completion of the reaction was checked by a Kaiser test. Next, the reaction solution was filtered and then subjected twice to deprotection reaction using 40 mL of 20% piperidine/DMF solution for 30 minutes each time. The reaction solution was filtered and washed three times with 40 mL of DMF and once with 40 mL of MC, thereby synthesizing H-Lys(Boc)-Arg(Pbf)Arg(Pbf)Arg(Pbf)Arg(Pbf)-CTL resin.

b. The H-Lys(Boc)-Arg(Pbf)Arg(Pbf)Arg(Pbf)Arg(Pbf)-CTL resin was wetted by adding a small amount of MC to the resin, and then 8.1 g (1.3 eq.) of Fmoc-His(Trt)-OH, 2.0 g (1.3 eq.) and 5.7 g (1.5 eq.) of HBTU, each dissolved in 20 mL of DMF, were added thereto and 5.2 mL (3 eq.) of DIPEA was added thereto, followed by reaction. After 4 hours of reaction, completion of the reaction was checked by a Kaiser test. Next, the reaction solution was filtered and subjected twice to deprotection reaction using 40 mL of 20% piperidine/DMF solution for 30 minutes each time. The reaction solution was filtered and washed three times with 40 mL of DMF and once with 40 mL of MC, thereby synthesizing H-His(Trt)Lys(Boc)-Arg(Pbf)Arg(Pbf)Arg(Pbf)Arg(Pbf)-CTL resin.

c. The H-His(Trt)Lys(Boc)-Arg(Pbf)Arg(Pbf)Arg(Pbf)Arg(Pbf)-CTL resin was wetted by adding MC to the resin. Then, 2.3 g (1.3 eq.) of Boc-Gly-OH, 2.0 g (1.3 eq.) of HOBt and 5.7 g (1.5 eq.) of HBTU, each dissolved in 20 mL of DMF, were added thereto and 5.2 mL (3 eq.) of DIPEA was added thereto, followed by reaction. After 4 hours of reaction, completion of the reaction was checked by a Kaiser test. Next, the reaction solution was filtered and washed three times with 40 mL of DMF and once with 40 mL of MC, thereby synthesizing Boc-GlyHis(Trt)Lys(Boc)-Arg(Pbf)Arg(Pbf)Arg(Pbf)Arg(Pbf)-CTL resin.

Example 3. Synthesis of Pal-GlyHis(Trt)Lys(Boc)-Arg(Pbf)Arg(Pbf)Arg(Pbf)Arg(Pbf)-CTL Resin a. A small amount of MC was added to the H-Arg(Pbf)Arg(Pbf)Arg(Pbf)Arg(Pbf)-CTL resin synthesized in Example 1, and then 6.1 g (1.3 eq.) of Fmoc-Lys(Boc)-OH, 2.0 g (1.3 eq.) of HOBt and 5.7 g (1.5 eq.) of HBTU, each dissolved in 20 mL of DMF, were added thereto and 5.2 mL (3 eq.) of DIPEA was added thereto, followed by reaction. After 4 hours of reaction, completion of the reaction was checked by a Kaiser test. Next, the reaction solution was filtered and subjected twice to deprotection reaction using 40 mL of 20% piperidine/DMF solution for 30 minutes each time. The reaction solution was filtered and washed three times with 40 mL of DMF and once with 40 mL of MC, thereby synthesizing H-Lys(Boc)-Arg(Pbf)Arg(Pbf)Arg(Pbf)Arg(Pbf)-CTL resin.

b. The H-Lys(Boc)-Arg(Pbf)Arg(Pbf)Arg(Pbf)Arg(Pbf)-CTL resin was wetted by adding a small amount of MC to the resin. Then, 8.1 g (1.3 eq.) of Fmoc-His(Trt)-OH, 2.0 g (1.3 eq.) of HOBt and 5.7 g (1.5 eq.) of HBTU, each dissolved in 20 mL of DMF, were added thereto and 5.2 mL (3 eq.) of DIPEA was added thereto, followed by reaction. After 4 hours of reaction, completion of the reaction was checked by a Kaiser test. Next, the reaction solution was filtered and subjected twice to deprotection reaction using 40 mL of 20% piperidine/DMF solution for 30 minutes each time. The reaction solution was filtered and washed three times with 40 mL of DMF and once with 40 mL of MC, thereby synthesizing H-His(Trt)Lys(Boc)-Arg(Pbf)Arg(Pbf)Arg(Pbf)Arg(Pbf)-CTL resin.

c. The H-His(Trt)Lys(Boc)-Arg(Pbf)Arg(Pbf)Arg(Pbf)Arg(Pbf)-CTL resin was wetted by adding MC to the resin. Then, 3.9 g (1.3 eq.) of Fmoc-Gly-OH, 2.0 g (1.3 eq.) of HOBt and 5.7 g (1.5 eq.) of HBTU, each dissolved in 20 mL of DMF, were added thereto and 5.2 mL (3 eq.) of DIPEA was added thereto, followed by reaction. After 3 hours of reaction, completion of the reaction was checked by a Kaiser test. Next, the reaction solution was filtered and then subjected twice to deprotection reaction using 40 mL of 20% piperidine/DMF solution for 30 minutes each time. The reaction solution was filtered and washed three times with 40 mL of DMF and once with 40 mL of MC, thereby synthesizing H-GlyHis(Trt)Lys(Boc)-Arg(Pbf)Arg(Pbf)Arg (Pbf)Arg(Pbf)-CTL resin.

d. The H-GlyHis(Trt)Lys(Boc)-Arg(Pbf)Arg(Pbf)Arg (Pbf)Arg(Pbf)-CTL resin was wetted by adding MC to the resin, and then 40 mL of DMF was added thereto. Next, 3.5 g (1.3 eq.) of palmitoyl chloride and 5.2 mL (3 eq.) of DIPEA were added thereto, followed by reaction. After 4 hours, the reaction was checked by a Kaiser test. After completion of the reaction, the reaction solution was filtered and then washed three times 40 mL of DMF and once with 40 mL of MC.

Example 4. Synthesis of H-ArgArgArgArg-OH (R4) (SEQ ID NO.: 2)

5% TFA/MC(ml) was added to the H-Arg(Pbf)Arg(Pbf) Arg(Pbf)Arg(Pbf)-CTL-resin synthesized in Example 1, and the resin was subjected to leaving reaction for 30 minutes. The filtrates that reacted three times were collected and concentrated, and then 50 mL of a solution of 95% TFA and 5% $H_2O$ was added thereto, stirred for 3 hours to remove the protecting group, and then concentrated. The filtrate was dispersed in ether, and crude R4 (SEQ ID NO.: 2) was recovered. The crude R4 (SEQ ID NO.: 2) peptide was dissolved in distilled water, and then purified using prep-LC (column ID 5 cm) and freeze-dried to obtain 1.7 g of white powder (99.1% purity (HPLC), 26.6% yield). The obtained powder had a molecular weight of 643.40 (M+1) (theoretical value: M=642.42) as measured by LC-MS.

Example 5. Synthesis of H-GlyHisLys-ArgArgArgArg-OH (GHK-R4) (SEQ ID NO.: 3)

5% TFA/MC(ml) was added to the Boc-GlyHis(Trt)Lys (Boc)-Arg(Pbf)Arg(Pbf)Arg(Pbf)Arg(Pbf)-CTL resin synthesized in Example 2, and the resin was subjected to leaving reaction for 30 minutes. The filtrates that reacted three times were collected and concentrated, and then 60 mL of a solution of 95% TFA and 5% $H_2O$ was added thereto, stirred for 4 hours to remove the protecting group, and then concentrated. The filtrate was dispersed in ether, and crude GHK-R4 (SEQ ID NO.: 3) was recovered. The crude GHK-R4 (SEQ ID NO.: 3) peptide was dissolved in distilled water, and then purified using prep-LC (column ID 5 cm) and freeze-dried to obtain 3.6 g of white powder (99.2% purity (HPLC), 37.3% yield). The obtained powder had a molecular weight of 965.60 (M+1) (theoretical value: M=964.59) as measured by LC-MS.

Example 6. Synthesis of Pal-GlyHisLys-ArgArgArgArg-OH (Pal-GHK-R4) (SEQ ID NO.: 4)

5% TFA/MC(ml) was added to the Pal-GlyHis(Trt)Lys (Boc)-Arg(Pbf)Arg(Pbf)Arg(Pbf)Arg(Pbf)-CTL resin synthesized in Example 3, and the resin was subjected to leaving reaction for 30 minutes. The filtrates that reacted three times were collected and concentrated, and then 60 mL of a solution of 95% TFA and 5% $H_2O$ was added thereto, stirred for 4 hours to remove the protecting group, and then concentrated. The filtrate was dispersed in ether, and crude Pal-GHK-R4 (SEQ ID NO.: 4) was recovered. The crude Pal-GHK-R4 (SEQ ID NO.: 4) peptide was dissolved in distilled water, and then purified using prep-LC (column ID 5 cm) and freeze-dried to obtain 3.4 g of white powder (99.5% purity (HPLC), 28.2% yield). The obtained powder had a molecular weight of 1203.80 (M+1) (theoretical value: M=1202.82) as measured by LC-MS.

Experimental Example 1. Toxicity Test for Novel Peptides

In order to examine the cytotoxicity of the novel peptides (GHK-R4 (SEQ ID NO.: 3) and Pal-GHK-R4 (SEQ ID NO.: 4)) according to the Examples of the present invention, MTT assay was performed. As a control, GHK-acetate was used. Fibroblasts were treated with various concentrations of each of the control and the novel peptides, and after 24 hours, treated with MTT reagent. Next, the absorbance was measured, and the viability of the cells was calculated based on the absorbance.

The results are shown in FIG. 1, and the three peptides all showed almost no cytotoxicity even at high concentrations. The $IC_{30}$ values were calculated to be about 31.71 mM for GHK-acetate, 5.32 mM for GHK-R4 (SEQ ID NO.: 3), and 8.70 μM for Pal-GHK-R4 (SEQ ID NO.: 4).

Experimental Example 2. Analysis of Intracellular Uptake of Novel Peptides

Figure 2:
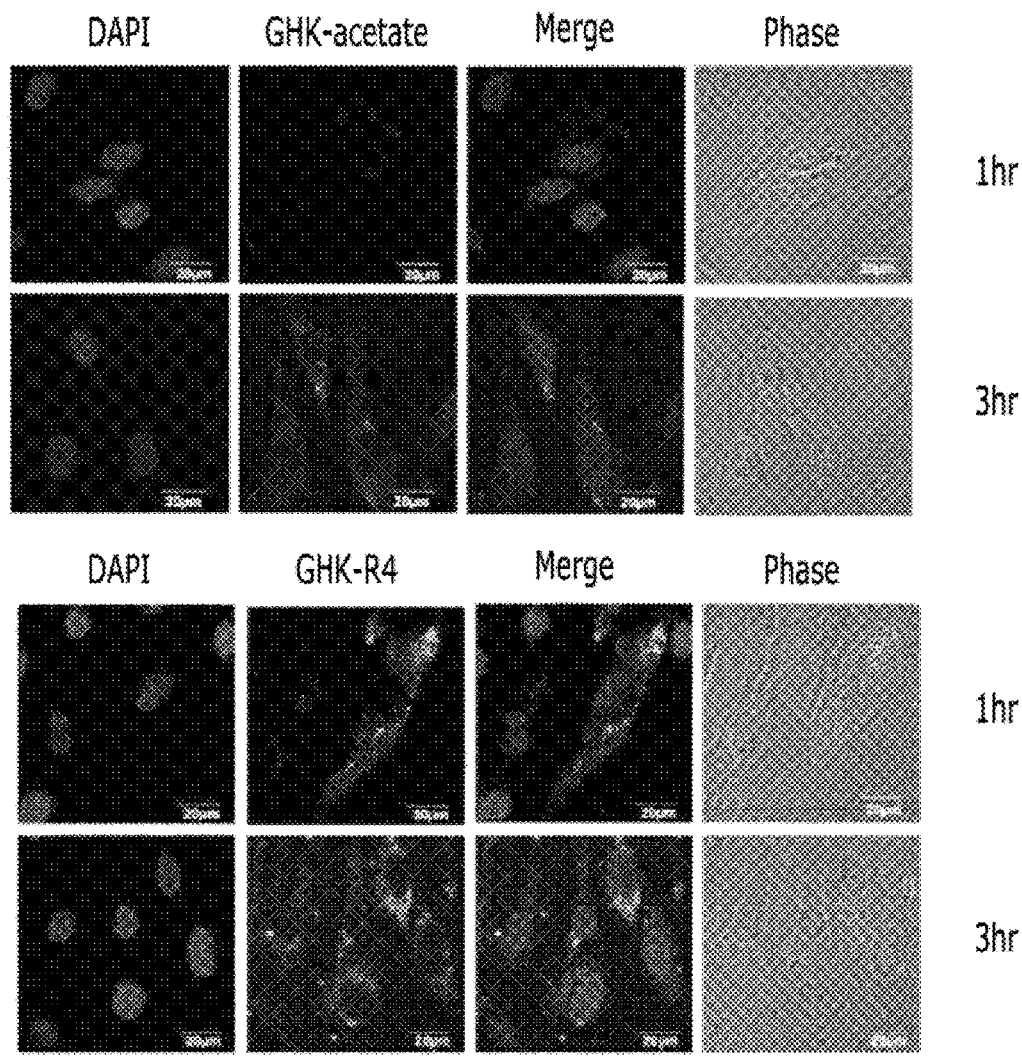
FIG. 2 compares intracellular uptake of GHK and the peptides of the present invention.

Hs68 fibroblasts were treated with 50 μM of each of GHK-acetate and GHK-R4 (SEQ ID NO.: 3) for 1 hour and 3 hours, and then intracellular uptake of each peptide was imaged by a confocal microscope. The results are shown in FIG. 2. It was confirmed that, when the fibroblasts were treated with GHK-acetate for 1 hour, almost no GHK-acetate entered the cytoplasm, and when the fibroblasts were treated with GHK-acetate for 3 hours, a portion of GHK-acetate entered the cytoplasm. On the contrary, it could be confirmed that GHK-R4 (SEQ ID NO.: 3) all entered the cytoplasm from 1 hour, and GHK-R4 (SEQ ID NO.: 3) entered the cells faster than GHK-acetate. That is, it was shown that, when R4 (SEQ ID NO.: 2) was attached to the carboxy-terminus of GHK (SEQ ID NO.: 3), the cell penetration rate and efficiency of the GHK-R4 (SEQ ID NO.: 3) increased.

Experimental Example 3. Analysis of Effects of Novel Peptides on UV-Induced MMP-2 Activity Gelatin zymography was performed to evaluate the effects of the novel peptides on UV-induced MMP-2 activity in UVB-irradiated Hs68 fibroblasts. MMP-2 is a protease that is increased when UV light or oxidative stress is applied to fibroblasts. Hs68 fibroblasts were treated with UVB to induce oxidative stress, and treated with various concentrations of each of the peptides, and then the activity of MMP-2 in the supernatant was measured. GHK-acetate, GHK-R4 (SEQ ID NO.: 3) and Pal-GHK-R4 (SEQ ID NO.: 4) all inhibited the UVB-induced MMP-2 activity, and specifically, GHK-R4 (SEQ ID NO.: 3) showed an MMP-2 inhibitory effect even at a concentration equal to about 1/10 of the concentration of GHK-acetate, and Pal-GHK-R4 (SEQ ID NO.: 4) showed an MMP-2 inhibitory effect even at a concentration equal to about 1/100 of the concentration of GHK-acetate (FIG. 3). That is, it was shown that, when R4 (SEQ ID NO.: 2) was attached to the carboxy-terminus of GHK, the GHK-R4 (SEQ ID NO.: 3) could inhibit UV-induced MMP-2 activity at a lower concentration, and when the palmitoyl group was attached thereto, the Pal-GHK-R4 (SEQ ID NO.: 4) could inhibit UV-induced MMP-2 activity at a lower concentration than the GHK-R4 (SEQ ID NO.: 3).

Experimental Example 4. Analysis of Effects of Novel Peptides on Collagen Synthesis The effects of the novel peptides on collagen synthesis in Hs68 fibroblasts irradiated with UVB were measured. After UVB irradiation, Hs68 fibroblasts were treated with various concentrations of each of the peptides, and the amount of soluble collagen secreted from the cells was measured using the supernatant. As a result, GHK-acetate, GHK-R4 (SEQ ID NO.: 3) and Pal-GHK-R4 (SEQ ID NO.: 4) all increased soluble collagen synthesis in a concentration-dependent manner compared to the UVB group. At this time, GHK-R4 (SEQ ID NO.: 3) increased collagen synthesis at a concentration equal to ⅕ of the concentration of GHK-acetate, and Pal-GHK-R4 (SEQ ID NO.: 4) increased collagen synthesis at a concentration equal to ¹/₁₀₀ of the concentration of GHK-acetate (FIG. 4), indicating that, when R4 (SEQ ID NO.: 2) or the palmitoyl group is attached to the carboxy-terminus of GHK, the GHK-R4 (SEQ ID NO.: 3) or the Pal-GHK-R4 (SEQ ID NO.: 4) can increase collagen synthesis, which decreased by UV rays, at lower concentrations than GHK.

Figure 5:
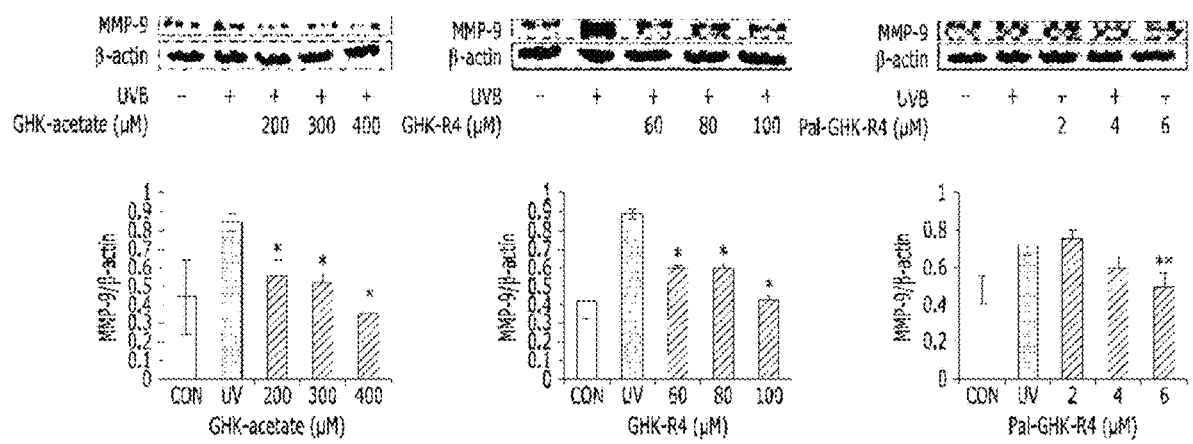
FIG. 5 shows the effects of GHK and the peptides of the present invention on MMP-9 activity in UV-irradiated cells.

Experimental Example 5. Analysis of Effects of Novel Peptides on UV-Induced MMP-9 Expression The effects of the novel peptides on changed expression of MMP-9 protein in Hs68 fibroblasts irradiated with UVB were analyzed by Western blotting. MMP-9 is a gelatinase which is a protease that is increased by ultraviolet rays or oxidative stress, like MMP-2. It was shown that, when cells were treated with each of GHK-acetate and the novel peptides after UVB irradiation, GHK-acetate and the novel peptides generally decreased the expression of MMP-9 in a concentration-dependent manner (FIG. 5), and in particular, GHK-R4 (SEQ ID NO.: 3) or Pal-GHK-R4 (SEQ ID NO.: 4) could inhibit the expression of MMP-9 at lower concentrations than GHK.

Taken together, the GHK tripeptide can be effectively introduced by linking polyarginine to the carboxy-terminus of the tripeptide, and the GHK-polyarginine can decrease UV-induced MMP-2/9 expression and increase collagen synthesis that decreased by UV rays, at lower concentrations than the GHK tripeptide. When a lipophilic group is covalently bonded to the GHK-polyarginine, intracellular penetration of the GHK-polyarginine-lipophilic group may further increase compared to that of the GHK-polyarginine, and the GHK-polyarginine-lipophilic group can inhibit negative effects, induced by UV rays, at lower concentrations than the GHK-polyarginine.

The above description of the present invention is exemplary, and those of ordinary skill in the art will appreciate that the present invention can be easily modified into other specific forms without departing from the technical spirit or essential characteristics of the present invention. Therefore, it should be understood that the exemplary embodiments described above are exemplary in all aspects and are not restrictive. For example, each component described to be of a single type can be implemented in a distributed manner. Likewise, components described to be distributed can be implemented in a combined manner.

The scope of the present invention is defined by the following claims. It shall be understood that all modifications and embodiments conceived from the meaning and scope of the claims and their equivalents are included within the scope of the present invention.

The invention claimed is:

1. A peptide for skin anti-aging and anti-wrinkle comprising: a glycine-histidine-lysine tripeptide; and polyarginine linked to the carboxy-terminus of the tripeptide,
   wherein a palmitoyl group is linked to the amino-terminus of the tripeptide, and
   wherein the polyarginine consists of four arginines linked together.

2. A composition for skin anti-aging and anti-wrinkle comprising the peptide according to claim 1.

3. The composition of claim 2, comprising 10 ppm to 100,000 ppm of the peptide.

4. The composition of claim 2, wherein the composition comprises 0.1 to 10 µM of the peptide.

5. The composition of claim 2, further comprising a pharmaceutically or cosmetically acceptable carrier.

6. The composition of claim 2, having a formulation selected from the group consisting of solution, external ointment, cream, foam, nutrient lotion, skin softener, pack, skin lotion, emulsion, makeup base, essence, soap, liquid cleanser, bath soak, sunscreen cream, sun oil, suspension, emulsion, paste, gel, lotion, powder, surfactant-containing cleanser, oil, powder foundation, emulsion foundation, wax foundation, patch, and spray formulations.

* * * * *

SEQUENCE LISTING

```
<160> NUMBER OF SEQ ID NOS: 4

<210> SEQ ID NO 1
<211> LENGTH: 12
<212> TYPE: PRT
<213> ORGANISM: Artificial Sequence
<220> FEATURE:
<223> OTHER INFORMATION: cell penetrating peptide

<400> SEQUENCE: 1

Lys Lys Lys Lys Lys Lys Lys Lys Lys Gly His Lys
1               5                   10

<210> SEQ ID NO 2
<211> LENGTH: 4
<212> TYPE: PRT
<213> ORGANISM: Artificial Sequence
<220> FEATURE:
<223> OTHER INFORMATION: cell penetrating peptide

<400> SEQUENCE: 2

Arg Arg Arg Arg
1

<210> SEQ ID NO 3
<211> LENGTH: 7
<212> TYPE: PRT
```

```
<213> ORGANISM: Artificial Sequence
<220> FEATURE:
<223> OTHER INFORMATION: cell penetrating peptide

<400> SEQUENCE: 3

Gly His Lys Arg Arg Arg Arg
1               5

<210> SEQ ID NO 4
<211> LENGTH: 8
<212> TYPE: PRT
<213> ORGANISM: Artificial Sequence
<220> FEATURE:
<223> OTHER INFORMATION: cell penetrating peptide
<220> FEATURE:
<221> NAME/KEY: UNSURE
<222> LOCATION: 1
<223> OTHER INFORMATION: lipophilic palmitoyl group attached to
      amino-terminus of GHKRRRR

<400> SEQUENCE: 4

Xaa Gly His Lys Arg Arg Arg Arg
1               5
```